United States Patent [19]

Chan et al.

[11] Patent Number: 5,595,995
[45] Date of Patent: Jan. 21, 1997

[54] PYRIDYL-PROPAN-2-YL ESTERS OF 1-ADAMANTANE CARBOXYLATES

[75] Inventors: Ferdinand Chan, Sutton; Michael Jarman, Tooting; Gerard A. Potter, Widnes, all of England

[73] Assignee: British Technology Group Limited, London, England

[21] Appl. No.: 335,743

[22] PCT Filed: Apr. 29, 1993

[86] PCT No.: PCT/GB93/00890

§ 371 Date: Jan. 18, 1995

§ 102(e) Date: Jan. 18, 1995

[87] PCT Pub. No.: WO93/23375

PCT Pub. Date: Nov. 25, 1993

[30] Foreign Application Priority Data

May 15, 1992 [GB] United Kingdom .................. 9210489
Nov. 12, 1992 [GB] United Kingdom .................. 9223738

[51] Int. Cl.$^6$ .......................... A61K 31/44; C07D 213/55
[52] U.S. Cl. ...................... 514/277; 546/285; 546/340; 546/342
[58] Field of Search .................... 546/285, 340, 546/342; 514/277

[56] References Cited

FOREIGN PATENT DOCUMENTS 0253681 1/1988 European Pat. Off. .
2428294 6/1974 Germany .

OTHER PUBLICATIONS

McCaque et al. "Inhibition of enzymes of estrongen . . . " Jour of Medicinal Chemistry, vol. 33 (1990), Washington, D.C. pp. 3050–3055.

D. Skwarski et al. "Sythesis of N–substituted . . . " Chemical Abstracts vol. 11 (No. 4) (14 Aug. 1989), Abstracts #57109g, p. 701. Acta Pol Pharm, 45 (4), 301–5.

CA 84(7)#43851e DE 2428294 (Merck) see formulae. (1976).

CA 79(23) #132815k & J. Med. Chem, 16(7), 865–7, see formulae. (1973).

CA 69(1) #2828z & J Med Chem. 11(2), 180–1. See formulae and anstract. (1968).

W. K. Amery et al., Drug Development Research, vol. 8, pp. 299–307, (1988).

M Ayub et al., Journal of Steroid Biochemistry, vol. 28, No. 5, pp. 521–531, (1987).

*Primary Examiner*—Alan L. Rotman
*Attorney, Agent, or Firm*—Nixon & Vanderhye

[57] ABSTRACT

Compounds having the general formula:

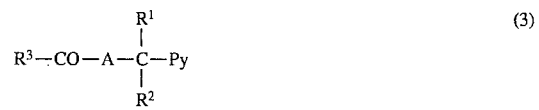

wherein each of $R^1$ and $R^2$ independently represents hydrogen or alkyl of 1 to 4 carbon atoms;

A represents —O— or —$CR^4R^5$, where $R^4$ and $R^5$ are defined as for $R^1$ or $R^2$;

$R^3$ represents an adamantyl group; and

Py represents a 3- or 4-pyridyl group, as free bases or their pharmaceutically acceptable salts are useful in treating androgen-dependent, especially prostatic, cancer.

10 Claims, No Drawings

PYRIDYL-PROPAN-2-YL ESTERS OF 1-ADAMANTANE CARBOXYLATES

This application is a 371 of PCT/GB93/00890 filed Apr. 29, 1993.

BACKGROUND OF THE INVENTION

1. Field of the invention

This invention relates to derivatives containing a 3- or 4-pyridyl group, namely 3- and 4-pyridylcarbinol esters of adamantanecarboxylic acid and adamantyl 2-(3- and 4-pyridyl)ethyl ketones, together with certain derivatives thereof, their preparation and use in treating prostatic cancer.

2. Description of related art

R. McCague, M. G. Rowlands, S. E. Bartie and J. Houghton, J. Med. Chem. 33, 3050–3055 (1990), have reported that certain esters of 4-pyridylacetic acid, of general formula:

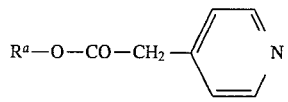
(1)

wherein $R^a$ represents a specified alicyclic group (e.g. cyclohexyl or a terpene residue) or

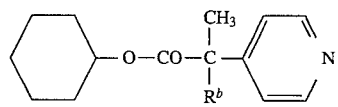
(2)

wherein $R^b$ represents a hydrogen atom or a methyl group, inhibit the 17α-hydroxylase/$C_{17-20}$ lyase enzyme complex which is essential for biosynthesis of androgens. The inhibition of androgen biosynthesis by virtue of the hydroxylase/lyase inhibition indicates that the compounds of McCague et al., supra, could be useful for the treatment of prostate cancer since many such tumours depend on androgens for growth.

The compounds of McCague et al. are also inhibitors of aromatase. Aromatase is an enzyme required in the biosynthesis of oestrogens. The ability to inhibit aromatase is considered a desirable property in compounds which are to be used to treat breast cancer. It is undesirable, however, for the treatment of prostatic cancer that a compound should be a strong inhibitor of both aromatase and hydroylase/lyase since the inhibition of aromatase would prevent the removal, by further conversion into oestrogens, of any products of the hydroxylase/lyase enzyme complex which escaped the blockade of hydroxylase/lyase. As a result, a patient could lose some of the benefits of hydroxylase/lyase inhibition. Accordingly, It is desirable to keep the lyase:aromatase inhibition ratio:

$$\frac{IC_{50} \text{ versus lyase}}{IC_{50} \text{ versus aromatase}}$$

as low as possible. (A small numerator indicates that the compound is a powerful inhibitor of lyase. A large denominator indicates that it is a poor inhibitor of aromatase). Further prior art, the relevance of which is apparent only after knowledge of the invention, is referred to below in a separate section.

SUMMARY OF THE INVENTION

It has now surprisingly been found that compounds of formula (3) below have useful hydroxylase/lyase inhibitory activity with low $IC_{50}$ lyase/aromatase ratios, and are therefore of potential value in treating androgen-dependent cancers such as prostatic cancer. These compounds have the general formula:

(3)

wherein each of $R^1$ and $R^2$ independently represents hydrogen or lower alkyl;

A represents —O—, or —$CR^4R^5$ where $R^4$ and $R^5$ are defined as for $R^1$ or $R^2$;

$R^3$ represents an adamantyl group; and

Py represents a 3- or 4-pyridyl group, as free bases or their pharmaceutically acceptable salts, especially acid addition salts. The term "lower" herein signifies that the group has 1 to 4 carbon atoms. The invention includes each of the optical isomers and mixtures thereof, especially racemic mixtures.

ADDITIONAL DESCRIPTION OF PRIOR ART

EP-A 253,681 (Farmatalia Carlo Erba) describes a class of compounds of formula

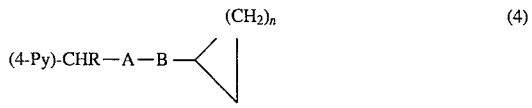
(4)

wherein 4-Py is the 4-pyridyl group, R is alkyl of 1–4 carbon atoms, —A—B— has a variety of meanings including the "reverse amide" linkage —NH—CO— and n is 1 to 5, preferably 4, i.e. the preferred cyclic group is cyclohexyl. These compounds are described as aromatase inhibitors useful, inter alia in the treatment of prostatic hyperplasia. However, applicants have found that these "reverse amides" of cyclohexanecarboxylic acid are POOR inhibitors of hydroxylase and lyase. Indeed, the reverse amide analogues of the compounds of formula (3), whereby A represents —NH— are LESS GOOD inhibitors than the compounds of formula (3). As shown in the Table, at the end of the Examples, the cyclohexanecarboxylic acid reverse amide had an $IC_{50}$ against lyase of 10 and against hydroxylase of 40, which are of the order of 20×greater than the less good compounds of formula (3), thus clearly showing a surprising advantage of the compounds of formula (3).

DE-OS 2,428,294 (Merck & Co. Inc) is a huge patent specification of 85 pages relating to compounds having a general formula broad enough to cover pyridyl thiomethyl esters of 1-adamantanecarboxylic acid of the narrower formula (5): Py—$CR^1R^2$—S—CO—$R^3$ wherein Py is the pyridine ring. $R^1$ and $R^2$ are hydrogen or alkyl of 1–3 carbon atoms and $R^3$ is adamantyl. However, such compounds are not exemplified and the closest Example (No. 26) relates to adamantyl-substituted 4-pyridylmethyl ethers. The compounds of this reference are said to be helpful in the treatment of rheumatoid arthritis.

W. Korytnyk and G Fricke, 3. Med. Chem. 11, 180–181 (1968) describe the synthesis of pyridoxol esters of 1-adamantanecarboxylic acid. These compounds, which are (4-methyl-5-hydroxy-6-hydroxymethyl)-3-pyridylmethyl and (2-hydroxy-3-methyl-6-hydroxymethyl-4-pyridylmethyl esters, and therefore have three pyridine ring substituents in addition to the adamantoyloxymethyl group, are described as weak growth inhibitors of a species of yeast. The first-mentioned compound is also reported by W. Korytnyk et al. in 3. Med. Chem. 16, 865–867 (1973) to reverse the acute toxicity in mice of 4-vinylpyridine.

DESCRIPTION OF THE PREFERRED EMBODIMENTS

The adamantyl group is preferably attached to the carbonyl group in formula (3) at a bridgehead (1-) position, as shown below in formula (6)

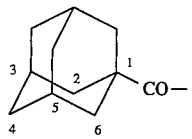
(6)

The invention includes optically active forms of the compounds of formula (3). For the chiral monomethyl compounds in the 4-pyridyl series ($R^1$=Me, R=H) the S-enantiomer is about 100 times more potent than the R-enantiomer, but surprisingly the dimethyl compound ($R^1$, $R^2$=Me), which would be expected to have activity around half-way between the R and S enantiomers, is almost equipotent to the active S-enantiomer.

The A group in formula (3) is preferably —O—, but when it is —$CH_2$— potentially hydrolysable ester bonds are not present, which is also advantageous.

All "lower alkyl" groups herein are preferably methyl or ethyl.

Preferably at least one of $R^1$ and $R^2$ represents alkyl, especially methyl and most preferably both are methyl.

In the ketones, $R^4$ and $R^5$ are preferably hydrogen, one is methyl and the other hydrogen or both are methyl.

The compounds of the invention can be prepared in various ways, conveniently starting from adamantanecarboxylic acid or a reactive derivative thereof. The starting compounds have the general formula $$R^3CO—X \quad (7)$$

wherein X represents —OH or a reactive substituent such as Cl or Br, or an ester residue and $R^3$ is as defined for formula (3). Reaction with an alcohol of formula (8), or the alkali metal alkoxide thereof,

(8)

where Py, $R^1$ and $R^2$ are as defined for formula (3) leads to the esters of formula (3).

To prepare the ketones of formula (3) in which A=—$CH_2$—, a suitable procedure involves the reaction between adamantyl methyl ketone enolate and a pyridylmethyl sulfonate derived from the alcohol of formula (8).

Alternatively ketones of formula (3) may be prepared by aldol condensation between an adamantyl alkyl ketone and a 3- or 4-pyridyl ketone or aldehyde of formula (9)

(9)

where $R^1$ is as defined for formula (3), and subsequent dehydration to give the enone (10)

(10)

where $R^1$, $R^3$ and $R^4$ and Py are as defined for formula (3) Conjugate addition of an alkylcuprate or copper hydride complex with (10) leads to ketones of formula (3).

The compounds may be prepared as salts, e.g. the hydrochloride and converted to the free base form and thereafter to such other conventional pharmaceutically acceptable salts as acetates, citrates and lactates, as may seem appropriate.

The present invention also provides a pharmaceutical composition which comprises a therapeutically effective amount of a compound of the invention, in association with a therapeutically acceptable carrier or diluent. The composition of the invention can, for example, be in a form suitable for parenteral (e.g. intravenous, intramuscular or intracavital), oral, topical or rectal administration. Particular forms of the composition may be, for example, solutions, suspensions, emulsions, creams, tablets, capsules, lipsomes or micro-reservoirs, especially compositions in orally ingestible or sterile injectable form. The preferred form of composition contemplated is the dry solid form, which includes capsules, granules, tablets, pills, boluses and powders. The solid carrier may comprise one or more excipients, e.g. lactose, fillers, disintegrating agents, binders, e.g. cellulose, carboxymethyl-cellulose or starch or anti-stick agents, e.g. magnesium stearate, to prevent tablets from adhering to tabletting equipment. Tablets, pills and boluses may be formed so as to disintegrate rapidly or to provide slow release of the active ingredient.

Where national patent law permits, the present invention also includes a method of treating androgen-dependent tumours in the mammalian body, especially prostatic tumours, which comprises administering a compound of the invention to a mammalian patient in a therapeutically effective dose, e.g. in the range 0.001–0.04 mmole/kg body weight, preferably 0.001–0.01 mmole/Kg, administered daily or twice daily during the course of treatment. This works out (for humans) at 20–800 mg/patient per day. Alternatively the invention includes the compounds of the invention for use in said treatment and their use in the manufacture of medicaments for that purpose.

The following Examples illustrate the invention. "Ether" means diethyl ether. "Petrol" refers to light petroleum (bp= 60°–80° C.). Concentrations for the solutions in which optical rotation is measured are in units of mol. $dm.^{-3}$. " B—" indicates a substituent attached to a boron atom. The symbol "ee" stands for enantiomeric excess as given by the expression $$\frac{[R]-[S]}{[R]+[S]} \times 100 \text{ where } [R] \text{ and } [S]$$

are relative proportions of R and S isomers. Thus, an R:S ratio of 9:1=ee of 80%.

EXAMPLE 1

4-Pyridylmethyl 1-adamantanecarboxylate

To 4-pyridylcarbinol (1.2 g, 11.0 mmol) in THF (40 ml) at −18° C. was added n-butyllithium (2.5 M, 4.2 ml, 10.5 mmol) in hexane dropwise with stirring. After 10 minutes a solution of 1-adamantanecarbonyl chloride (2.0 g, 10.0 mmol) in THF (10 ml) was added and stirring continued at room temperature for 30 minutes. The mixture was poured into water, basified with saturated aqueous sodium bicarbonate, and extracted with ether. The ether extracts were combined, dried (Na$_2$CO$_3$) and concentrated, Chromatography, on elution with petrol-ether-triethylamine 100:50:1, gave the title compound (0.95 g, 35%), which crystallised from 60–80 petrol, m.p. 57°–58° C., IR ν$_{max}$ 1730 cm$^{-1}$; $^1$H-NMR(CDCl$_3$) δ1.74 and 1.96 (12H, 2s, adamantyl CH$_2$), 2.05 (3H, s, adamantyl CH), 5.12 (2H, s, OCH$_2$), 7.24 (2H, d, J 5.7 Hz, Py 3 and 6H), 8.60 (2H, d, J 5.7 Hz, Py 2 and 6H). Anal. Calcd: C, 75.24; H, 7.80; N, 5.16. Found: C, 75.34; H, 7.92; N, 5.04%.

EXAMPLE 2

(+)-(R)-1-(4-Pyridyl)ethyl 1-adamantanecarboxylate

The method followed that described in Example 1, but using (+)-(R)-1-(4-pyridyl)ethanol (369 mg, 3.0 mmol) in THF (12 ml), n-butyllithium (2.5 M, 1.2 ml, 3.0 mmol) in hexane, and 1-adamantanecarbonyl chloride (656 mg, 3.3 mmol) in THF (3 ml). Chromatography, on elution with petrol-ether-triethylamine 200:50:1, afforded the title compound (754 mg, 88%). [α]$_D$ +25.8° (c 1, CHCl$_3$); IR ν$_{max}$ 1730 cm$^{-1}$; $^1$H-NMR (CDCl$_3$) δ1.50 (3H, d, J 6.6 Hz, CHCH$_3$), 1.73 and 1.93 (12H, 2s, adamantyl CH$_2$), 2.04 (3H, s, adamantyl CH), 5.80 (1H, q, J 6.6 Hz, OCH), 7.23 (2H, d, J 6.1 Hz, Py 3 and 5H), 8.58 (2H, d, J 6.1 Hz, Py 2 and 6 H); MS m/z 285 (M$^+$). By passing hydrogen chloride gas through a solution of the product in ether, the hydrochloride was obtained, m.p. 164°–166° C. Anal. Calcd: C, 67.17; H, 7.52; N, 4.35. Found: C, 67.58; H, 7.51; N, 4.36%.

EXAMPLE 3

(−)-(S)-1-(4-Pyridyl)ethyl 1-adamantanecarboxylate

The method was the same as for Example 2, but using (−)-(S)-1-(4-pyridyl)ethanol (369 mg, 3.0 mmol), and provided the title compound (774 mg, 90%). [α]$_D$ −24.4° (c 1, CHCl$_3$); IR, NMR and MS data were the same as given in Example 2. The hydrochloride had m.p. 164°–166° C.

EXAMPLE 4 a) 2-(4-Pyridyl)propan-2-ol

A solution of methyllithium (1.4 M; 30 ml, 42 mmol) in diethyl ether was added dropwise to a stirred solution of 4-acetylpyridine (4.65 ml, 42 mmol) in dry THF (100 ml) at −76° C., and the deep blue solution allowed to reach ambient temperature. After 24 hours the mixture was partitioned between ether and saturated aqueous sodium bicarbonate, and the ether phase was concentrated. Chromatography, on elution with ethyl acetate-dichloromethane-triethylamine 60:40:1, gave the title compound (2.59 g, 45%) as an oil. $^1$H-NMR (CDCl$_3$) δ1.58 (6H, s, CMe$_2$), 7.40 (2H, d, J 6.2 Hz, Py 3 and 5-H), 8.55 (2H, d, J 6.2 Hz, Py 2 and 6-H); MS m/z 137 (M$^+$).

b) 2-(4-Pyridyl)propan-2-yl 1-adamantanecarboxylate

The method followed that described in Example 1, but using 2-(4-pyridyl)propan-2-ol (0.69 g, 5.0 mmol) in THF (20 ml), n-butyllithium (2.5 M; 2.0 ml, 5.0 mmol) in hexane, and 1-adamantanecarbonyl chloride (1.09 g, 5.5 mmol) in THF (6 ml). Chromatography, on elution with ether-petrol-triethylamine 50:50:1, gave the title compound (1.06 g, 71%) as an oil. IR ν$_{max}$ 1730 cm$^{-1}$; $^1$H-NMR (CDCl$_3$) δ1.71 (6H, s, CMe$_2$), 1.71 and 1.90 (12H, 2s, adamantyl CH$_2$), 2.02 (3H, s, adamantyl CH), 7.23 (2H, d, J 6.1 Hz, Py 3 and 5-H), 8.56 (2H, d, J 6.1 Hz, Py 2 and 6-H). Anal. Calcd: C, 76.22; H, 8.42; N, 4.68. Found: C, 76.17; H, 8.47; N, 4.64%.

EXAMPLE 5

3-Pyridylmethyl 1-adamantanecarboxylate

The method followed that described in Example 1, but using 3-pyridylcarbinol (240 mg, 2.2 mmol) in THF (10 ml), n-butyllithium (2.5 M; 0.84 ml, 2.1 mmol) in hexane, and 1-adamantanecarbonyl chloride (397 mg, 2.0 mmol) in THF (2 ml). Chromatography, on elution with petrol-ether-triethylamine 200:50:1, gave the title compound (422 mg, 78%) as an oil. IR ν$_{max}$ 1728 cm$^{-1}$; $^1$H-NMR (CDCl$_3$) δ1.71 and 1.91 (12H, 2s, adamantyl CH$_2$), 2.02 (3H, s, adamantyl CH), 5.11 (2H, s, OCH$_2$), 7.30 (1H, m, Py 5-H), 7.66 (1H, m, Py 4-H), 8.56 (1H, m. Py 6-H), 8.61 (1H, m, Py 2-H). Anal. Calcd: C, 75.24; H, 7.80; N, 5.16. Found: C, 75.09; H, 7.84; N, 5.03%.

EXAMPLE 6

(+)-(R)-1-(3-Pyridyl)ethyl 1-adamantanecarboxylate

The method followed that described in Example 1, but using (+)-(R)-1-(3-pyridyl)ethanol [87% ee; prepared by asymmetric reduction of 3-acetylpyridine with (+)-B-chlorodiisopinocampheyl borane, J. Chandrasekharan, P. V. Ranachandran and H. C. Brown, J. Org. Chem., 50, 5446–5448 (1985)] (0.62 g, 5.0 mmol) in THF (20 ml), n-butyllithium (2.5 M; 2.0 ml, 5.0 mmol) in hexane, and 1-adamantanecarbonyl chloride (1.09 g, 5.5 mmol) in THF (5 ml). Chromatography, on elution with ether-petrol-triethylamine 100:50:1, gave the title compound (1.16 g, 81%) as an oil. [α]$_D$ +29.9° (c 2, MeOH), 87% ee. Recrystallisation of the (−)-(1R)-10-camphorsulfonate salt from ethyl acetate, and reliberation of the free-base, afforded the title compound with 98% ee, [α]$_D$ +33.7° (c 2, MeOH). IR ν$_{max}$ 1728 cm$^{-1}$; $^1$H-NMR (CDCl$_3$) δ1.54 (3H, d, J 6.5 Hz, CHCH$_3$), 1.72 and 1.90 (12H, 2s, adamantyl CH$_2$), 2.03 (3H, s, adamantyl CH), 5.88 (1H, q, J 6.5 Hz, CHCH$_3$), 7.30 (1H, m, Py 5-H), 7.65 (1H, m, Py 4-H), 8.56 (1H, m, Py 6-H), 8.63 (1H, m, Py 2-H); MS m/z 285 (M$^+$). Anal. Calcd: C, 75.76; H, 8.12; N, 4.91. Found: C, 75.30; H, 8.18; N, 4.46%.

EXAMPLE 7

(−)-(S)-1-(3-Pyridyl)ethyl 1-adamantanecarboxylate The method followed that described in Example 1, but using (−)-(S)-1-(3-pyridyl)ethanol [80% ee; prepared by asymmetric reduction of 3-acetylpyridine with (−)-B-chlorodiisopinocampheyl borane] (0.49 g, 4.0 mmol) in THF (16 ml), n-butyllithium (2.5 M; 1.6 ml, 4.0 mmol) in hexane, and 1-adamantanecarbonyl chloride (0.87 g, 4.4 mmol) in THF (4 ml). Work-up and chromatography, as described in Example 6, afforded the title compound (0.92 g, 81%) as an oil. [α]$_D$ −27.6° (c 2, MeOH), 80% ee. Recrystallisation of the (+)-(1S)-10-camphorsulfonate salt, and reliberation of the free-base, afforded the title compound with 95% ee, [α]$_D$ −32.7° (c 2, MeOH). IR, NMR and MS data were the same as given in Example 6.

EXAMPLE 8 a) 2-(3-Pyridyl)propan-2-ol

The method followed that of Example 4a, but using methyllithium (1.4 M; 14 ml, 20 mmol) in diethyl ether and 3-acetylpyridine (2.2 ml, 20 mmol) in dry THF (40 ml). Work-up and chromatography, on elution with ether-petrol-triethylamine 30:10:1, afforded the title compound (1.26 g, 46%) as an oil. $^1$H-NMR (CDCl$_3$) δ1.58 (6H, s, CMe$_2$), 7.22 (1H, m, Py 5-H), 7.85 (1H, m, Py 4-H), 8.32 (1H, m, Py 6-H), 8.65 (1H, m, Py 2-H); MS m/z 137 ( M$^+$).

b) 2-(3-Pyridyl)propan-2-yl 1-adamantanecarboxylate

The method followed that of Example 4b, but using 2-(3-pyridyl)propan-2-ol (0.69 g, 5.0 mmol), and provided the title compound (1.06 g, 71%) as an oil. IR $v_{max}$ 1730 cm$^{-1}$; $^1$H-NMR (CDCl$_3$) δ1.71 (6H, s, CMe$_2$), 1.77 and 1.94 (12H, 2s, adamantyl CH$_2$), 2.02 (3H, s, adamantyl CH), 7.25 (1H, m, Py 5-H), 7.65 (1H, m, Py 4-H), 8.48 (1H, m, Py 6-H), 8.63 (1H, m, Py 2-H). Anal. Calcd: C, 76.22; H, 8.42; N, 4.68. Found: C, 75.87; H, 8.52; N, 4.34%.

EXAMPLE 9

1-(1-Adamantyl)-3-(3-pyridyl)propan-1-one

To a stirred solution of 3-pyridylmethanol (0.29 ml, 3.0 mmol) in dry THF (20 ml) at 0° C. was added butyllithium (1.6 M; 1.87 ml, 3.0 mmol) in hexane followed after 5 minutes by p-toluenesulfonyl chloride (0.57 g, 3.0 mmol) and stirring continued for 1 hour. In a separate flask butyllithium (1.6 M; 5.63 ml, 9.0 mmol) in hexane was added to a stirred solution of diisopropylamine (1.26 ml, 9.0 mmol) in dry THF (40 ml) at 0° C. followed after 5 minutes by 1-adamantyl methyl ketone (1.60 g, 9.0 mmol). After stirring for 30 minutes at 0° C. the resulting solution of the lithium enolate of 1-adamantyl methyl ketone was then added to the solution of 3-pyridylmethyl p-toluenesulfonate and the clear solution allowed to attain room temperature. After 18 hours the mixture was partitioned between diethyl ether and water, and the ether layers were concentrated. Chromatography gave, on elution with 150:100:1 ether-petrol-triethylamine, the title compound (0.52 g, 65%) as an oil, which was further purified by short-path (Kugelrohr) distillation at 225° C. and 0.2 mm Hg. IR $v_{max}$ 1697 cm$^{-1}$; H-NHR (CDCl$_3$) δ1.68–1.77 (12H, m, adamantyl CH$_2$), 2.02 (3H, s, adamantyl CH), 2.74–2.91 (4H, m, COCH$_2$CH$_2$), 7.21 (1H, m, Py 5-H), 7.51 (1H, m, Py 4-H), 8.43 (1H, m. Py 6-H), 8.46 (1H, m, Py 2-H); MS m/z 269 (M$^+$). Anal. Calcd: C, 80.26; H, 8.61; N, 5.20. Found: C, 80.04; H, 8.71; N, 5.07%.

EXAMPLE 10

(±)-1-(1-Adamantyl)-3-(3-pyridyl)butan-1-one

The method essentially followed that described in Example 9, but using (±)-1-(3-pyridyl)ethanol (0.37 g, 3.0 mmol). Chromatography, on elution with ether-petrol-triethylamine 125:50:1, afforded the title compound (0.35 g, 41%) as an oil. IR $v_{max}$ 1698 cm$^{-1}$; $^1$H-NMR (CDCl$_3$) δ1.25 (3H, d, J 6.9 Hz, CHCH$_3$), 1.71–1.81 (12H, m, adamantyl CH$_2$), 2.02 (3H, s, adamantyl CH), 2.74–2.77 (2H, m, COCH$_2$), 7.21 (1H, m, Py 5-H), 7.51 (1H, m, Py 4-H), 8.43 (1H, m, Py 6-H), 8.50 (1H, m, Py 2-H); MS m/z 283 (M$^+$). Anal. Calcd: C, 80.52; H, 8.89; N, 4.94. Found: C, 80.38; H, 8.87; N, 4.74%.

EXAMPLE 11

(±)-1-(1-Adamantyl)-2-methyl-3-(3-pyridyl)propan-1-one

To a stirred solution of diisopropylamine (0.42 ml, 3.0 mmol) in THF (10 ml) at 0° C. was added butyllithium (1.6M; 1.87 ml, 3.0 ml) in hexane followed after 5 minutes by a solution of 1-(1-adamantyl)-3-(3-pyridyl)propan-1-one in THF (8 ml). After stirring for a further 20 min at 0° C., methyl iodide (0.19 ml, 3.0 mmol) was added dropwise and the solution was allowed to attain room temperature. After 1 hr the mixture was partitioned between ether and water. The ether extracts were dried (Na$_2$CO$_3$) and concentrated. Chromatography on elution with petrol-ether-triethylamine 100:50:1 afforded the title compound (0.62g, 73%), which crystallised from pentane, m.p 69–70 C; IR $v_{max}$ 1696 cm$^{-1}$; $^1$H-NMR (CDCl$_3$) δ1.06 (3H,d,J 6.7 Hz, CHCH$_3$) 1.51–1.72 (12H, m, adamantyl CH$_2$), 1.96 (3H, s, adamantyl CH), 2.57 and 2.92 (2H, m, CHCH$_2$), 3.28 (1H, m, CHCH$_3$), 7.18 (1H, m, Py 5-H), 7.43 (1H, m, Py 4-H), 8.43 (2H, m, Py 6-H and 2-H); MS m/z 283 (M$^+$). Anal. Calcd: C, 80.52; H, 8.89; N, 4.94. Found: C, 80.56; H, 8.95; N, 4.91%.

EXAMPLE 12

(+)-(S)-1-(1-Adamantyl)-3-(3-pyridyl)butan-1-one

The method essentially followed that described in Example 9 but using (−)-(S)-1-(3-pyridyl)ethanol [91% e.e; prepared by asymmetric reduction of 3-acetylpyridine with (+)-B-chlorodiisopinocampheylborane] (0.37g, 3.0 mmol). Chromatography, on elution with petrol-ether-triethylamine 125:50:1, afforded the title compound (0.35g, 41%) as an oil. 81% ee, [α]$_D$+12.50° (c 0.8, MeOH). IR, NMR and MS data were the same as given in Example 10.

EXAMPLE 13

(−)-(R)-1-(1-Adamantyl)-3-(3-pyridyl)butan-1-one

The method essentially followed that of Example 9 but using (+)-(R)-1-(3-pyridyl)ethanol (91% ee; 0.37 g, 3.0 mmol). Chromatography, on elution with petrol-ether-triethylamine 125:50:1, afforded the title compound (0.33 g, 39%) as an oil. 83% ee, [α]$_D$−12.8° (c 0.8, MeOH). IR, NMR and MS data were the same as given in Example 10.

EXAMPLE 14

(±)-1-(1-Adamantyl)-3-(4-pyridyl)butan-1-one

The method followed that described in Example 9 but using (±)-1-(4-pyridyl)ethanol (0.37 g, 3.0 mmol). Chromatography, on elution with petrol-ether-triethylamine 100:50:1, gave the title compound (153 mg, 18%), which crystallised from hexane. m.p. 100°–101° C.; IR $v_{max}$ 1698 cm$^{-1}$; $^1$H-NMR (CDCl$_3$) δ1.22 (3H, d, CHCH$_3$), 1.62–1.81 (12H, m, adamantyl CH$_2$), 2.02 (3H, s, adamantyl CH), 2.72 (2H, m, COCH$_2$), 3.37 (1H, m, CHCH$_3$), 7.15 (2H, d, J 6.1 Hz, Py 3-H and 5-H), 8.49 (2H, d, J 6.1 HZ, Py 2-H and 6-H); MS m/z 283 (M$^+$). Anal. Calcd: C, 80.52; H, 8.89; N, 4.94. Found: C, 80.38; H, 8.99; N, 4.87%.

EXAMPLE 15

(+)-(S)-1-(1-Adamantyl)-3-(4-pyridyl)butan-1-one

The method followed that described in Example 9 but using (−)-(S)-1-(4-pyridyl)ethanol (1.84 g, 15.0 mmol) in THF (80 ml), butyllithium (1.6M; 9.4 ml, 15.0 mmol) in hexane, p-toluenesulfonyl chloride (2.86 g, 15.0 mmol), diisopropylamine (6.31 ml, 45.0 mmol) in THF (120 ml), butyllithium (1.6M; 28.12 ml, 45.0 mmol) in hexane and 1-adamantyl methyl ketone (8.0 g, 45 mmol). Chromatography, on elution with petrol-ether-triethylamine 100:50:1 gave the title compound (765 mg, 18%), which crystallised from hexane. m.p. 46°–48° C.; [α]$_D$+6.8° (c 1.0, MeOH). IR, NMR and MS data were the same as given in Example 14.

EXAMPLE 16

(−)-(R)-1-(1-Adamantyl)-3-(4-pyridyl)butan-1-one

The method followed that described in Example 9 but using (+)-(R)-1-(4-pyridyl)ethanol (1.84 g, 15.0 mmol) in THF (80 ml), butyllithium (1.6M; 9.4 ml, 15.0 mmol) in hexane, p-toluenesulfonyl chloride (2.86 g, 15.0 mmol), diisopropylamine (6.31 ml, 45.0 mmol) in THF (120 ml), butyllithium (1.6M; 28.12 ml, 45.0 mmol) in hexane and 1-adamantyl methyl ketone (8.0 g, 45 mmol). Chromatography, on elution with petrol-ether-triethylamine 100:50:1 gave the title compound (722 mg, 17%), which crystallised from hexane, m.p. 48°–49° C.; $[\alpha]_D$ –6.6° (c 1.0, MeOH). IR, NMR and MS data were the same as given in Example 14.

EXAMPLE 17

This Example illustrates an alternative method for preparing the compound already prepared in Example 10.

a) trans-1-(1-Adamantyl)-3-(3-pyridyl)-2-propen-1-one

To a stirred solution of diisopropylamine (1.54 ml, 11 mmol) in THF (40 ml) at 0° C. was added butyllithium (1.6M; 6.25 ml, 10.0 mmol) in hexane, followed after 5 minutes by 1-adamantyl methyl ketone (1.96 g, 11.0 mmol). After stirring for 30 minutes at 0° C. the resulting solution of the lithium enolate of 1-adamantyl methyl ketone was then added to a stirred solution of 3-pyridinecarboxaldehyde (0.94 ml, 10.0 mmol) in THF (12 ml) at room temperature. After 3 hours the mixture was partitioned between diethyl ether and water, and the ether layers were concentrated. Chromatography, on elution with petrol-ether-triethylamine, 100:50:1 afforded the product as a solid (1.87 g, 70%), which crystallised from hexane, m.p. 98°–101° C.; IR $v_{max}$ 1679 cm$^{-1}$; $^1$H-NMR (CDCl$_3$) δ1.65–1.84 (12H, m, adamantyl CH$_2$), 2.10 (3H, s, adamantyl CH), 7.27 (1H, d, J 15.8 Hz, COCHCH), 7.38 (1H, m, Py 5-H), 7.68 (1H, d, J 15.8 Hz, COCHCH), 7.93 (1H, m, Py 4-H), 8.55 (1H, m, Py 6-H), 8.81 (1H, m, Py 2-H); MS m/z 267 (M$^+$).

b) (±)-1-(1-Adamantyl)-3-(3-pyridyl)butan-1-one (via conjugate addition)

To a suspension of cuprous bromide-dimethylsulfide (1.28 g, 6.25 mmol) in THF (20 ml) cooled to –18° C., was added dropwise methyllithium (1.4 M; 8.93 ml, 12.5 mmol) in ether. The resulting clear solution was left to stir for a further 45 minutes before a solution of 1-(1-adamantyl)-3-(3-pyridyl)-2-propen-1-one (1.34 g, 5.0 mmol) in THF (8 ml) was added at –18° C. After 4 hours at 0° C. the reaction mixture was quenched with aqueous ammonium hydroxide solution and extracted with ether. The ether extracts were combined, dried (Na$_2$CO$_3$) and concentrated. Chromatography, on elution with petrol-ether-triethylamine 125:50:1, provided the title compound (1.16 g, 82%) as an oil. Analytical data were the same as given in Example 10.

EXAMPLE 18

This Example illustrates an alternative method for preparing the compound already prepared in Example 14.

a) trans-1-(1-Adamantyl)-3-(4-pyridyl)-2-propen-1-one

The method essentially followed that described in Example 17a but using 4-pyridinecarboxaldehyde (0.48 ml, 5.0 mmol) in THF (6 ml), diisopropylamine in THF (20 ml), butyllithium (3.13 g, 5.0 mmol) and 1-adamantyl methyl ketone (0.48 ml, 5.0 mmol). Chromatography, on elution with petrol-ether-triethylamine 100:100:1, gave the title compound (881 mg, 66%), which crystallised from hexane, m.p. 128°–129° C., IR $v_{max}$ 1690 cm$^{-1}$; $^1$H-NMR (CDCl$_3$) δ1.72–1.89 (12H, adamantyl CH$_2$) 2.12 (3H, s, adamantyl CH), 7.36 (1H, d, J 15.6 Hz, COCHCH), 7.56 (1H, d, J 15.6 Hz, COCHCH), 7.71 (2H, d, J 5.5 Hz, Py 3-H and 5-H), 8.71 (2H, d, J 5.5 Hz, Py 2-H and 6-H); MS m/z 267 (M$^+$). Anal. Calcd: C, 80.86; H, 7.92; N, 5.24. Found: C, 80.96; H, 8.13; N, 5.04 %.

b) (±)-1-(1-Adamantyl)-3-(4-pyridyl)butan-1-one (via conjugate addition)

The method essentially followed that desribed in Example 17b but using 1-(1-Adamantyl)-3-(4-pyridyl)-2-propen-1-one (1.34 g, 5.0 mmol). Chromatography, on elution with petrol-ether-triethylamine 100:50:1, provided the title compound (1.0 g, 71%), which crystallised from hexane, m.p. 100°–101° C. Analytical data were the same as given in Example 14.

The following Table shows the activities of the compounds prepared in Examples 1–10 as inhibitors of aromatase, lyase and hydroxylase. Also included, for comparison, are "reverse amide" analogues of formula (3) and a cyclohexanecarboxylic acid reverse amide compound according to EP-A 253,681 above.

TABLE $$R^3-CO-A-\underset{\underset{R^2}{|}}{\overset{\overset{R^1}{|}}{C}}-Py \quad (11); R^3 = \text{"Ad" or "Cy"}$$

| Ex | R$^3$ | A | R$^1$ | R$^2$ | Py | R/S | Aromatase | Lyase | Hydroxylase |
|---|---|---|---|---|---|---|---|---|---|
| 1 | Ad | O | H | H | 4 | — | 0.58 | 0.025 | 0.04 |
| 2 | " | O | Me | H | 4 | R | 16.1 | 0.06 | 0.3 |
| 3 | " | O | H | Me | 4 | S | 5.6 | 0.0015 | 0.003 |
| 4 | " | O | Me | Me | 4 | — | 20.5 | 0.002 | 0.009 |
| 5 | " | O | H | H | 3 | — | 8.0 | 0.5 | 1.5 |
| 6 | " | O | Me | H | 3 | R | 35.6 | 0.15 | 0.6 |
| 7 | " | O | H | Me | 3 | S | 4.6 | 0.2 | 0.8 |
| 8 | " | O | Me | Me | 3 | — | 50.7 | 0.09 | 0.4 |
| 9 | " | CH$_2$ | H | H | 3 | — | 3.4 | 0.45 | 2.2 |
| 10 | " | CH$_2$ | Me | H | 3 | rac. | 1.4 | 0.5 | 1.3 |
| 11 | " | CHMe | H | H | 3 | rac. | 2.7 | 0.7 | 1.0 |
| — | " | NH | H | H | 4 | — | 1.5 | 1.4 | 6.8 |
| — | " | NH | H | H | 3 | — | 32.5 | 20 | 70 |
| — | Cy | NH | H | H | 4 | — | n.d. | 10 | 40 |

IC$_{50}$ (μM) applies to Aromatase, Lyase, Hydroxylase columns.

n.d. = not determined; rac. = racemic mixture.

The methods of assay used in connection with the Table are substantially as described for the majority of compounds in GB-A 2,253,851, using human sources of the enzymes. Thus, for hydroxylase determinations, the microsomal preparation, prepared according to S. E. Bartie et al., 3. Steroid Biochem. 33, 1191–1195 (1979) which refers back to F. 1. Chasalow, 3. Biol. Chem. 254, 3000–3005 (1979), in 50 mM sodium phosphate buffer, pH 7.4, was added to the other components of the reaction mixture. The mixture consisted of 250 μM NADPH, 10 mM D-glucose 6-phosphate, 3U/ml. D-glucose 6-phosphate dehydrogenase, 1 mM MgCl$_2$, 0.1 mM dithiothreitol, 0.2 mM EDTA, 3 μM $^3$H-progesterone (1 mCi/μmol), 50 mM sodium phosphate buffer pH 7.4, the compound under test dissolved in 50% DMSO, 1% DMSO (final concentration), 1% ethanol and the microsomal preparation diluted with the buffer, in a total volume of 100 μl.

Changes from GB-A 2,253,851 are as follows:

In the hydroxylase assay, the "Nucleosil" pre-column for separation of steroids was also "C18". In the lyase assay, the reaction was stopped after ½ hour. In the HPLC, ignore the diameter given for the PELL column, the "Ecoscint A" contained 5% methanol and 5% acetonitrile (not 10% methanol). The enzyme activity was measured from 3 (not 4) concentrations of compound.

The resistance of the esters of Examples 1–8 to hydrolytic cleavage was measured by the method of R. McCague et al., (1990) supra. It was found that the compounds of Examples 4 and 8 in which $R^1=R^2=$methyl were considerably more resistant to cleavage than the other esters. These compounds also had low lyase:aromatase inhibition ratios.

We claim:

1. A compound having the following formula:

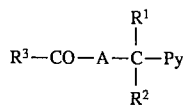

(3)

wherein each of $R^1$ and $R^2$ independently represents hydrogen or alkyl of 1 to 4 carbon atoms;

A represents —O—, or $CR^4R^5$ where $R^4$ and $R^5$ are defined as for $R^1$ or $R^2$;

$R^3$ represents an adamantyl group; and

Py represents a 3- or 4-pyridyl group, as a free base or a pharmaceutically acceptable salts thereof.

2. A compound according to claim 1 wherein A represents —O— or —$CH_2$—.

3. A compound according to claim 1 wherein $R^3$ represents an adamantyl group of the following formula:

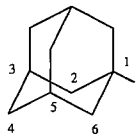

4. A compound according to claim 1 wherein at least one substituent selected from the group consisting of $R^1$, $R^2$, $R^4$ and $R^5$ is a methyl group.

5. A compound according to claim 1, wherein at least one of $R^1$ and $R^2$ represents an alkyl group of 1 to 4 carbon atoms.

6. A compound according to claim 5 wherein $R^1$ and $R^2$ represent methyl groups.

7. A pharmaceutical composition comprising an effective amount of a compound claimed in claim 1, in association with a therapeutically acceptable carrier or diluent.

8. A method of treating a patient suffering from androgen-dependent prostatic cancer, which comprises administering to said patient an effective dose of a compound claimed in claim 1.

9. 2-(4-Pyridyl)propan-2-yl 1-adamantanecarboxylate or a pharmaceutically acceptable salts thereof.

10. A method of treating a patient suffering from androgen-dependent prostatic cancer, which comprises administering to said patient an effective dose of 2-(4-pyridyl)propan-2-yl 1-adamantanecarboxylate or a pharmaceutically acceptable salt thereof.

* * * * *